United States Patent

Moldt et al.

Patent Number: 5,801,174
Date of Patent: Sep. 1, 1998

[54] FUSED INDOLE AND QUINOXALINE DERIVATIVES, THEIR PREPARATION AND USE

[75] Inventors: Peter Moldt, Humlebaek; Frank Wätjen, Herlev, both of Denmark

[73] Assignee: Neurosearch A/S, Glostrup, Denmark

[21] Appl. No.: 809,086

[22] PCT Filed: Sep. 12, 1995

[86] PCT No.: PCT/EP95/03594

§ 371 Date: May 20, 1997

§ 102(e) Date: May 20, 1997

[87] PCT Pub. No.: WO96/08495

PCT Pub. Date: Mar. 21, 1996

[30] Foreign Application Priority Data

Sep. 14, 1994 [DK] Denmark .................. 1054/94

[51] Int. Cl.[6] .................. C07D 487/04; C07D 471/04; A61K 31/435; A61K 31/495
[52] U.S. Cl. .................. 514/253; 540/557; 544/345; 546/84; 548/433; 514/217; 514/292; 514/411
[58] Field of Search .................. 540/557; 544/345; 546/84; 548/433; 514/217, 253, 292, 411

[56] References Cited

FOREIGN PATENT DOCUMENTS

0529636A1  3/1993  European Pat. Off.
WO9409000  4/1994  WIPO

*Primary Examiner*—Zinna Northington Davis
*Attorney, Agent, or Firm*—Birch, Stewart, Kolasch & Birch, LLP

[57] ABSTRACT

The present patent application discloses compounds having the formula

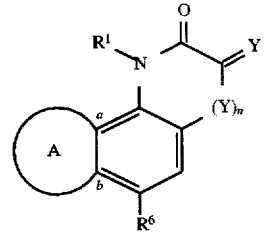

or a pharmaceutically acceptable salt thereof
wherein
$R^1$ is hydrogen, alkyl or benzyl;
X is O or $NOR^2$, wherein $R^2$ is hydrogen, alkyl or benzyl;
Y is $N-R^4$ wherein $R^4$ is hydrogen, OH or alkyl;
n is 0 or 1;
$R^6$ is phenyl which is substituted one or more times with substituents selected from the group consisting of $SO_2NR'R''$, $CONR'R''$, and $COR'''$
wherein R' and R" each independently are hydrogen, alkyl, or $-(CH_2)_p-W$, wherein p is 0, 1, 2, 3, 4, 5, or 6, and W is hydroxy, amino, alkoxycarbonyl, or phenyl which may be substituted one or more times with substituents selected from the group consisting of halogen, $CF_3$, $NO_2$, amino, alkyl, alkoxy or methylenedioxy; or wherein R' and R" together is $(CH_2)_rZ(CH_2)_s$, wherein r and s each independently are 0, 1, 2, 3, 4, 5, or 6 and Z is O, S, $CH_2$ or NR"" wherein R"" is hydrogen, alkyl, or $-(CH_2)_p-W$, wherein p is 0, 1, 2, 3, 4, 5, or 6, and W is hydroxy, amino, alkoxycarbonyl, or phenyl which may be substituted one or more times with substituents selected from the group consisting of halogen, $CF_3$, $NO_2$, amino, alkyl, alkoxy or methylenedioxy; and wherein R'" is hydrogen, alkyl, alkoxy or phenyl which may be substituted one or more times with substituents selected from the group consisting of halogen, $CF_3$, $NO_2$, amino, alkyl, alkoxy or methylenedioxy;

A is a ring of five to seven atoms fused with the benzo ring at the positions marked a and b.

The compounds are useful in the treatment of cerebrovascular disorders for example.

14 Claims, 1 Drawing Sheet

FUSED INDOLE AND QUINOXALINE DERIVATIVES, THEIR PREPARATION AND USE

The present application is a U.S. national stage application filed under 35 U.S.C. §371 of International Application PCT/EP95/03594, filed on Sept. 12, 1995.

The present invention relates to novel ring fused compounds capable of antagonising the biological effects of excitatory amino acids, such as glutamate, a method of treatment therewith, pharmaceutical compositions comprising the compounds and to a method of preparing the novel compounds of the invention.

OBJECT OF THE INVENTION

It is an object of the present invention to provide novel glutamate antagonists which are useful in the treatment of disorders or diseases in mammals, including a human, and especially in the treatment of disorders or diseases which are responsive to glutamate and or aspartate receptor antagonists.

Another object of the present invention is to provide a method of treating disorders or diseases of mammals, including a human, responsive to glutamic and/or aspartic acid receptor antagonists which comprises administering to a mammal in need thereof a compound of the invention.

A third object of the present invention is to provide novel pharmaceutical compositions for the treatment of disorders or diseases of mammals, including a human, responsive to glutamic and/or aspartic acid receptor antagonists.

Other objectives of the present invention will be apparent to the skilled person hereinafter.

BACKGROUND OF THE INVENTION

Excessive excitation by neurotransmitters can cause the degeneration and death of neurons. It is believed that this degeneration is in part mediated by the excitotoxic actions of the excitatory amino acids (EAA), glutamate and aspartate, at the N-methyl-D-aspartate (NMDA), the 2-amino-3-(3-hydroxy-5-methylisoxazol-4-yl)- propionic acid (AMPA) receptor, and the kainate receptor. This excitotoxic action is responsible for the loss of neurons in cerebrovascular disorders such as cerebral ischemia or cerebral infarction resulting from a range of conditions, such as thromboembolic or haemorrhagic stroke, cerebral vasospasm, hypoglycaemia, cardiac arrest, status epilepticus, perinatal asphyxia, anoxia such as from near-drowning, pulmonary surgery and cerebral trauma as well as lathyrism, Alzheimer's, and Huntington's diseases.

The compounds of the present invention may also be useful in the treatment of Amyotrophic Lateral Sclerosis (ALS), schizophrenia, Parkinsonism, epilepsy, anxiety, pain and drug addiction.

SUMMARY OF THE INVENTION

The invention then, inter alia, comprises the following, alone or in combination:

A compound having the formula or a pharmaceutically acceptable salt thereof
wherein
$R^1$ is hydrogen, alkyl or benzyl;
X is O or $NOR^2$, wherein $R^2$ is hydrogen, alkyl or benzyl;
Y is N—$R^4$ wherein $R^4$ is hydrogen, OH or alkyl;
n is 0 or 1;
$R^6$ is phenyl which is substituted one or more times with substituents selected from the group consisting of $SO_2NR'R''$, $CONR'R''$, and $COR'''$
wherein R' and R'' each independently are hydrogen, alkyl, or —$(CH_2)_p$—W, wherein p is 0, 1, 2, 3, 4, 5, or 6, and W is hydroxy, amino, alkoxycarbonyl, or phenyl which may be substituted one or more times with substituents selected from the group consisting of halogen, $CF_3$, $NO_2$, amino, alkyl, alkoxy or methylenedioxy; or wherein R' and R'' together is $(CH_2)_r Z(CH_2)_s$ wherein r and s each independently are 0, 1, 2, 3, 4, 5, or 6 and Z is O, S, $CH_2$ or NR'''' wherein R'''' is hydrogen, alkyl, or —$(CH_2)_p$—W, wherein p is 0, 1, 2, 3, 4, 5, or 6, and W is hydroxy, amino, alkoxycarbonyl, or phenyl which may be substituted one or more times with substituents selected from the group consisting of halogen, $CF_3$, $NO_2$, amino, alkyl, alkoxy or methylenedioxy; and wherein R'''' is hydrogen, alkyl, alkoxy or phenyl which may be substituted one or more times with substituents selected from the group consisting of halogen, $CF_3$, $NO_2$, amino, alkyl, alkoxy or methylenedioxy;

A is a ring of five to seven atoms fused with the benzo ring at the positions marked a and b, and formed by the following bivalent radicals:

wherein
$R^{12}$ is hydrogen, $CH_2CH_2OH$, or alkyl;

a compound as above having the formula or a pharmaceutically acceptable salt thereof;
wherein X, Y, n, R¹, R⁶, and R¹² have the meanings set forth above;

a compound as above having the formula or a pharmaceutically acceptable salt thereof;
wherein X, Y, n, R¹, R⁶, and R¹² have the meanings set forth above;

a compound as above having the formula or a pharmaceutically acceptable salt thereof;
wherein X, Y, n, R¹, R⁶, and R¹² have the meanings set forth above;

a compound as any above which is
8-methyl-5-(4-(N,N-dimethylsulphamoyl)phenyl)-6,7,8, 9-tetrahydro-1H-pyrrolo[3,2h]- isoquinoline-2,3-dione-3-oxime,
b 8-methyl-5-(4-(sulphamoyl)phenyl)-6,7,8,9-tetrahydro-1H-pyrrolo[3,2-h]-isoquinoline- 2,3-dione-3-oxime,
8-methyl-5-(4-(N,N-bis(2-hydroxyethyl)sulphamoyl)phenyl)-6,7,8,9-tetrahydro-1H -pyrrolo[3,2-h]isoquinoline-2,3-dione-3-oxime,
8-methyl-5-(4-(ethoxycarbonyl)phenyl)-6,7,8,9-tetrahydro-1H-pyrrolo[3,2-h]-isoquinoline -2,3-dione-3-oxime.
8-methyl-5-(4-(N,N-dimethylsulphamoyl)phenyl)-6,7,8,9-tetrahydro-1H-pyrrolo[3,2h]-isoquinoline-2,3-dione-3-O-methyloxime,
8-methyl-5-(4-(N-t-butylsulphamoyl)phenyl)-6,7,8,9-tetrahydro-1H-pyrrolo[3,2-h]-isoquinoline-2,3-dione-3-oxime,
8-methyl-5-(4-(morpholinosulfonyl)phenyl)-6,7,8,9-tetrahydro-1H-pyrrolo[3,2-h]-isoquinoline-2,3-dione-3-oxime,
8-methyl-5-(4-(N-(2-hydroxyethyl)sulphamoyl)phenyl)-6, 7,8,9-tetrahydro-1H-pyrrolo[3,2-h]isoquinoline-2,3-dione-3-oxime,
8-methyl-5-(4-(N,N-dimethylcarbamoyl)phenyl)-6,7,8,9-tetrahydro-1H-pyrrolo[3,2-h]-isoquinoline-2,3-dione-3-oxime,
8-methyl-5-(4-(4-(2-hydroxyethyl)piperazinosulfonyl)phenyl)-6,7,8,9-tetrahydro-1H -pyrrolo[3,2-h]-isoquinoline-2,3-dione-3-oxime,
8-methyl-5-(4-(N,N-dimethylsulphamoyl)phenyl)-6,7,8,9-tetrahydro-1H-pyrrolo[3,2h]- isoquinoline-2,3-dione-3-O-t-butyloxime,
8-methyl-5-(4-(morpholinosulfonyl)phenyl)-6,7,8,9-tetrahydro- 1H-pyrrolo[3,2-h]-isoquinoline-2,3-dione,
8-methyl-5-(4-(N,N-di(2-(N,N-diethylamino)ethyl)-sulphamoyl)-phenyl)-6,7,8,9-tetrahydro -1H-pyrrolo[3,2-h]-isoquinoline-2,3-dione-3-oxime,
8-methyl-5-(4-(piperidinosulfonyl)-phenyl)-6,7,8,9-tetrahydro-1H-pyrrolo[3,2-h]-isoquinoline-2,3-dione-3-oxime,
8-methyl-5-(4-(N-phenylsulphamoyl)-phenyl)-6,7,8,9-tetrahydro-1H-pyrrolo[3,2-h]-isoquinoline-2,3-dione-3-oxime,
8-methyl-5-(4-(N,N-diethylsulphamoyl)-phenyl)-6,7,8,9-tetrahydro-1H-pyrrolo[3,2-h]-isoquinoline-2,3-dione-3-oxime,
8-methyl-5-(4-(N-methyl-N-(2-(N,N-dimethylamino)-ethyl)sulphamoyl)-phenyl)-6,7,8,9-tetrahydro-1H-pyrrolo[3,2-h]isoquinoline-2,3-dione-3-oxime,
8-methyl-5-(4-(4-(4-chlorophenyl)piperazinosulfonyl)-phenyl)-6,7,8,9-tetrahydro-1H -pyrrolo[3,2-h]-isoquinoline-2, 3-dione-3-oxime,
8-methyl-5-(4-(4-(3,4-methylenedioxybenzyl)-piperazinosulfonyl)phenyl)-6,7,8,9-tetrahydro -1H-pyrrolo[3,2-h]-isoquinoline-2,3-dione-3-oxime,
8-methyl-5-(4-(N-(ethoxycarbonylmethyl)sulphamoyl)-phenyl)-6,7,8,9-tetrahydro-1H-pyrrolo[3,2-h]isoquinoline-2,3-dione-3-oxime,
7-methyl-5-(4-(morpholinosulfonyl)phenyl)-6,7,8,9-tetrahydro-1H-pyrrolo[2, 3-f]isoquinoline -2,3-dione-3-oxime,
7-methyl-5-(4-(morpholinosulfonyl)phenyl)-6,7,8,9-tetrahydro-1H-pyrrolo[2, 3-f]-isoquinoline -2,3-dione-3-O-methyloxime,
7-ethyl-5-(4-(morpholinosulfonyl)phenyl)-1,6,7,8-tetrahydrobenzo[1,2-b:3,4-c]dipyrrole-2,3-dione-3-oxime,
7-ethyl-5-(4-(N,N-dimethylsulphamoyl)phenyl)-1,6,7,8-tetrahydrobenzo[1,2-b:3,4-c]dipyrrole-2,3-dione-3-oxime,
8-methyl-5-(4-(N,N-dibenzylsulphamoyl)-phenyl)-6,7,8,9-tetrahydro-1H-pyrrolo[3,2h]-isoquinoline-2,3-dione-3-oxime, the corresponding 2,3-diones
or a pharmaceutically acceptable salt thereof;
a method of treating a disorder or disease of a mammal, including a human, which disorder or disease is responsive to glutamic and/or aspartic acid receptor antagonists, which comprises administering to a patient in need thereof an effective amount of a compound as any above;
a method as above wherein lathyrism, Alzheimer's disease, Huntington's diseases, ALS, schizophrenia, Parkinsonism, epilepsy, anxiety, pain, drug addiction, or cerebrovascular disorders are treated;
a pharmaceutical composition comprising a therapeutically-effective amount of a compound as any above together with at least one pharmaceutically-acceptable carrier or diluent;
the use of a compound as any above for the manufacture of a medicament for the treatment a disorder or disease of a mammal, including a human, which disorder or disease is responsive to glutamic and/or aspartic acid receptor antagonists;
the use of a compound as above for the manufacture of a medicament for the treatment of lathyrism, Alzheimer's disease, Huntington's diseases, ALS, schizophrenia, Parkinsonism, epilepsy, anxiety, pain, drug addiction, or cerebrovascular disorders; and a method of preparing a compound as any above comprising the step of:

a) reacting a compound having the formula wherein A, a, b $R^1$, Y, n and $R^6$ have the meanings set forth above, with $NH_2OR^2$, wherein $R^2$ has the meaning set forth above, or with a reactive derivative thereof, to form a compound of the invention; or b) reacting a compound having the formula wherein A, a, b $R^1$, and $R^6$ have the meanings set forth above, with oxalic acid or a reactive derivative thereof, to form a compound of the invention, or c) reacting a compound having the formula wherein A, a, b, and $R^6$ have the meanings set forth above, with chloral or a reactive derivative thereof, to form a compound of the invention.

Examples of pharmaceutically acceptable addition salts include inorganic and organic acid addition salts such as the hydrochloride, hydrobromide, phosphate, nitrate, perchlorate, sulphate, citrate, lactate, tartrate, maleate, fumarate, mandelate, benzoate, ascorbate, cinnamate, benzenesulfonate, methanesulfonate, stearate, succinate, glutamate, glycollate, toluene-p-sulphonate, formate, malonate, naphthalene-2-sulphonate, salicylate and the acetate. Such salts are formed by procedures well known in the art.

Other acids such as oxalic acid, while not in themselves pharmaceutically acceptable, may be useful in the preparation of salts useful as intermediates in obtaining compounds of the invention and their pharmaceutically acceptable acid addition salts.

Halogen is fluorine, chlorine, bromine, or iodine.

Alkyl means a straight chained or branched chain of from one to six carbon atoms or cyclic alkyl of from three to seven carbon atoms, including but not limited to, methyl, ethyl, propyl, isopropyl, butyl, isobutyl, t-butyl, pentyl, hexyl, cyclopropyl, cyclobutyl, cyclopentyl, cyclohexyl; methyl, ethyl, propyl and isopropyl are preferred groups.

Alkoxy is O-alkyl, wherein alkyl is as defined above.

Amino is $NH_2$ or NH-alkyl or N-(alkyl)$_2$, wherein alkyl is as defined above.

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention exist in (+) and (−) forms as well as in racemic forms. Racemic forms can be resolved into the optical antipodes by known methods, for example, by separation of diastereomeric salts thereof, with anoptically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallization of d- or l- (tartrates, mandelates, or camphorsulphonate) salts for example. The compounds of the present invention may also be resolved by the formation of diastereomeric amides by reaction of the compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the compounds of the present invention with an optically active chloroformate or the like.

Additional methods for the resolvation of optical isomers, known to those skilled in the art may be used, and will be apparent to the average skilled in the art. Such methods include those discussed by J. Jaques, A. Collet, and S. Wilen in "Enantiomers, Racemates, and Resolutions", John Wiley and Sons, New York (1981).

Furthermore, as the compounds of the invention are oximes they can exist in two forms, syn- and anti-form, depending on the arrangement of the substituents around the —C=N—double bond. The present invention includes both the syn and anti-form of the compounds of the invention as well as mixtures thereof. Acids catalyzes anti-syn isomerization.

Starting materials for the processes described in the present application are known or can be prepared by conventional methods from commercially available chemicals.

The products of the reactions described herein are isolated by conventional means such as extraction, crystallization, distillation, chromatography, and the like.

Biological Activity

The compounds of the invention exhibit valuable biological properties because of their strong excitatory amino acid (EAA) antagonizing properties at the AMPA ((RS)-alfa-amino-3-hydroxy-5-methyl-4-isoxazolepropionic acid) binding site.

In Vitro activity (receptor affinity):

The compounds of the present invention exhibit binding affinity for the AMPA receptor as described by T. Honoré et al., Neuroscience Letters 54, 27–32 (1985) with $IC_{50}$ values from the nanomolar to the lower micro molar range, see table 1.

The compounds of the invention have also been tested for their ability to inhibit GABA release from cultured cerebral cortex neurons in the following test:

³H-GABA Release, Cortical Neurons

Background: Neurons which express receptors for excitatory amino acids can be depolarized by such compounds and this depolarization will ultimately lead to a release of transmitter substance from the neurons. Cultured neurons obtained from 15-day-old mouse embryo cortex are mainly GABAergic and express all types of excitatory amino acid receptors. This means that they can be stimulated by high potassium or by the excitatory amino acids, NMDA, AMPA and kainate to release their neurotransmitter GABA.

³H-GABA may be used to label the GABA transmitter pool in the neurons and the release of ³H-GABA from the neurons may be used as a simple functional model for studies of the effects of excitatory amino acids and their antagonists.

Method: Cerebral cortices of 16-day-old mouse embryos are chopped in 0.4×0.4 mm cubes. The tissue is dissociated by mild trypsinization (0.1% (wt/vol) trypsin, 37° C., 15 min) and subsequently inoculated into poly-L-lysine-coated 3-cm Petri dishes containing a slightly modified DMEM (24.5 mM KCl, 30 mM glucose) supplemented with p-aminobenzoate (7 µM), insulin (100 mU/L) and 10% (vol/vol) horse serum. Cells are maintained in culture for 5–7 days with the addition of the antimitotic agent cytosine arbinoside (40 µM) from day 2 in vitro to prevent glial profileration. For further details and references, see Drejer et al. Exp. Brain Res. 47, 259 (1982).

Release experiments are performed using the model described by Drejer et al. Life Sci. 38, 2077 (1986). Cerebral cortex neurons cultured in Petri dishes (30 mm) are added 100 µM γ-vinyl-GABA one hour before the experiment in order to inhibit degradation of GABA in the neurons. 30 min before the experiment 5 µCi ³H-GABA is added to each culture and after this preloading period the cell monolayer at the bottom of the dish is covered with a piece of nylon mesh to protect the cells against mechanical damage and to facilitate dispersion of medium over the cell layer. The preloading medium is removed and the Petri dishes are placed in a superfusion system consisting of a peristaltic pump continously delivering thermostated 37° C. superfusion medium HEPES buffered saline (HBS): 10 mM HEPES, 135 mM NaCl, 5 mM KCl, 0.6 mM MgSO$_4$, 1.0 mM CaCl$_2$ and 6 mM D-glucose; pH 7.4) from a reservoir to the top of the slightly tilted Petri dish. The medium is continously collected from the lower part of the dish and delivered to a fraction collector. Initially, the cells are superfused with HBS for 15 min (flow rate 2 ml/min). Then the cells are stimulated for 30 sec every 4 min by changing the superfusion medium from HBS to a corresponding medium containing antagonists.

Test subtances are dissolved in 50% DMSO, 48% ethanol. The final DMSO and ethanol concentration in the assay must not exceed 0.1%.

The stimulated release of ³H-GABA (cpm) are corrected for the mean basal release(cpm) before and after stimulation.

The stimulated release in the presence of antagonists are expressed relative to the stimulated release and the IC$_{50}$ value for the antagonist is calculated (the concentration (µM) of the test substance which inhibit 50% of the stimulated ³H-GABA release).

The test results obtained by testing the compounds of the invention for their in-vitro AMPA receptor affinity and their ability to inhibit GABA release are presented in the following table:

TABLE 1

| Compound | Binding IC$_{50}$ (µM) | GABA release IC$_{50}$ (µM) |
|---|---|---|
| 8-methyl-5-(4-(N,N-dimethylsulphamoyl)-phenyl)-6,7,8,9-tetrahydro-1H-pyrrolo[3,2-h]-isoquinoline-2,3-dione-3-oxime | 0.020 | 0.12 |
| 8-methyl-5-(4-(sulphamoyl)phenyl)-6,7,8,9-tetrahydro-1H-pyrrolo[3,2-h]isoquinoline-2,3-dione-3-oxime | 0.025 | 0.27 |
| 8-methyl-5-(4-(N,N-bis(2-hydroxyethyl)sulphamoyl)-phenyl)-6,7,8,9-tetrahydro-1H-pyrrolo[3,2-h]-isoquinoline-2,3-dione-3-oxime | 0.050 | 0.13 |
| 8-methyl-5-(4-(ethoxycarbonyl)phenyl)-6,7,8,9 tetrahydro-1H-pyrrolo[3,2-h]-isoquinoline-2,3-dione-3-oxime | 0.10 | 3.70 |
| 8-methyl-5-(4-(N,N-dimethylsulphamoyl)-phenyl)-6,7,8,9-tetrahydro-1H-pyrrolo[3,2-h]-isoquinoline-2,3-dione-3-O-methyloxime | 0.20 | 1.70 |
| 8-methyl-5-(4-(N-t-butylsulphamoyl)-phenyl)-6,7,8,9-tetrahydro-1H-pyrrolo[3,2-h]-isoquinoline-2,3-dione-3-oxime | 0.03 | 0.24 |
| 8-methyl-5-(4-(morpholinoslfonyl)-phenyl)-6,7,8,9-tetrahydro-1H-pyrrolo[3,2-h]-isoquinoline-2,3-dione-3-oxime | 0.04 | 0.03 |
| 8-methyl-5-(4-(N-(2-hydroxyethyl)sulphamoyl)-phenyl)-6,7,8,9-tetrahydro-1H-pyrrolo[3,2-h]-isoquinoline-2,3-dione-3-oxime | 0.04 | 0.33 |
| 8-methyl-5-(4-(N,N-dimethylcarbamoyl)-phenyl)-6,7,8,9-tetrahydro-1H-pyrrolo[3,2-h]-isoquinoline-2,3-dione-3-oxime | 0.14 | 0.19 |
| 8-methyl-5-(4-(4-(2-hydroxyethyl)piperazinosulfonyl)-phenyl)-6,7,8,9-tetrahydro-1H-pyrrolo[3,2-h]-isoquinoline-2,3-dione-3-oxime | 0.019 | 0.1 |
| 8-methyl-5-(4-(N,N-dimethylsulphamoyl)-phenyl)-6,7,8,9-tetrahydro-1H-pyrrolo[3,2-h]-isoquinoline-2,3-dione-3-O-t-butyloxime | 0.47 | 5.5 |
| 8-methyl-5-(4-(morpholinosulfonyl)-phenyl)-6,7,8,9-tetrahydro-1H-pyrrolo[3,2-h]-isoquinoline-2,3-dione | 0.82 | 2.16 |
| 8-methyl-5-(4-(N,N-di(2-(N,N-diethylamino)ethyl)-sulphamoyl)-phenyl)-6,7,8,9-tetrahydro-1H-pyrrolo[3,2-h]-isoquinoline-2,3-dione-3-oxime | 0.038 | 0.45 |
| 8-methyl-5-(4-(piperidinosulfonyl)-phenyl)-6,7,8,9-tetrahydro-1H-pyrrolo[3,2-h]-isoquinoline-2,3-dione-3-oxime | 0.027 | 0.24 |
| 8-methyl-5-(4-(N-phenylsulphamoyl)-phenyl)-6,7,8,9-tetrahydro-1H-pyrrolo[3,2-h]-isoquinoline-2,3-dione-3-oxime | 0.066 | 0.38 |
| 8-methyl-5-(4-(N,N-diethylsulphamoyl)-phenyl)-6,7,8,9-tetrahydro-1H-pyrrolo[3,2-h]-isoquinoline-2,3-dione-3-oxime | 0.018 | 0.16 |
| 8-methyl-5-(4-(N-methyl-N-(2-(N,N-dimethylamino)-ethyl)sulphamoyl)-phenyl)-6,7,8,9-tetrahydro-1H-pyrrolo[3,2-h]-isoquinoline-2,3-dione-3-oxime | 0.19 | 0.31 |
| 8-methyl-5-(4-(4-(4-chlorophenyl)piperazinosulfonyl)-phenyl)-6,7,8,9-tetrahydro-1H-pyrrolo[3,2-h]-isoquinoline-2,3-dione-3-oxime | 0.068 | 0.877 |
| 8-methyl-5-(4-(4-(3,4-methylenedioxybenzyl)-piperazinosulfonyl)phenyl)-6,7,8,9-tetrahydro-1H-pyrrolo[3,2-h]-isoquinoline-2,3-dione-3-oxime | 0.13 | 0.50 |
| 8-methyl-5-(4-(N-(ethoxycarbonylmethyl)-sulphamoyl)phenyl)-6,7,8,9-tetrahydro-1H-pyrrolo[3,2-h]isoquinoline-2,3-dione-3-oxime | 0.034 | 0.34 |
| 7-methyl-5-(4-(morpholinosulfonyl)phenyl)-6,7,8,9-tetrahydro-1H-pyrrolo[2,3-f]isoquinoline-2,3-dione-3-oxime | 0.11 | 0.25 |
| 7-methyl-5-(4-(morpholinosulfonyl)phenyl)-6,7,8,9-tetrahydro-1H-pyrrolo[2,3-f]isoquinoline-2,3-dione-3-O-methyloxime | 0.22 | 1.6 |

TABLE 1-continued

| Compound | Binding IC$_{50}$ (µM) | GABA release IC$_{50}$ (µM) |
|---|---|---|
| 7-ethyl-5-(4-(morpholinosulfonyl)phenyl)-1,6,7,8-tetrahydrobenzo[1,2-b:3,4-c]dipyrrole-2,3-dione-3-oxime | 0.14 | 0.50 |
| 7-ethyl-5-(4-(N,N-dimethylsulphamoyl)-1,6,7,8-tetrahydrobenzo[1,2-b:3,4-c]dipyrrole-2,3-dione-3-oxime | 1.6 | 4.5 |
| 8-methyl-5-(4-(N,N-dibenzylsulphamoyl)-phenyl)-6,7,8,9-tetrahydro-1H-pyrrolo[3,2-h]-isoquinoline-2,3-dione-3-oxime | 0.54 | 1.9 |

The compound, 8-methyl-5-(4(N,N-dimethylsulphamoyl)-phenyl)-6,7,8,9-tetrahydro-1H-pyrrolo[3,2-h]isoquinoline-2,3-dione-3-oxime has also been tested for its ability to inhibit the clonic seizures induced by AMPA in the following test:

In Vivo activity (AMPA-induced clonic seizures)

AMPA given icv (intracerebroventricular) (15 µg/kg) to NMRI mice induces clonic seizures which should be inhibited by non-NMDA receptor antagonists. Method: Test compound was given i.v. 5 min (or p.o. 30 min) before a 0.3 µg icv administration of AMPA to 10 female NMRI mice (weighing 24–26 g) per dose. The number of mice experiencing clonic seizures within the next 5 min was noted. An ED$_{50}$ value was calculated as the dose inhibiting 50% of the mice from having clonic seizures.

TABLE 2

| Compound | ED$_{50}$ (mg/kg) |
|---|---|
| 8-methyl-5-(4-(N,N-dimethylsulphamoyl)-phenyl)-6,7,8,9-tetrahydro-1H-pyrrolo[3,2-h]-isoquinoline-2,3-dione-3-oxime | 3 |

The compound, 8-methyl-5-(4-(N,N-dimethylsulphamoyl)-phenyl)-6,7,8,9-tetrahydro-1H-pyrrolo[3,2-h]isoquinoline-2,3-dione-3-oxime has also been tested in the following animal model of global ischaemia:

Transient Forebrain Ischemia Model (2-VO Gerbils)

Gerbils were anaesthetized with halothane, right and left carotid arteries located and occluded for 4 minutes. Animals were kept warm before and after the operation using heating lamps. During the operation the gerbils were placed on heating plates, body temperature controlled and maintained at 37°±0.5° C. Postocclusion, the gerbils were divided in two groups. One group received 30 mg/kg test compound i.p. 30, 60, and 90 min post occlusion (total dose was 90 mg/kg). The control group received 5.5% glucose i.p. at the same time intervals. Four days later, the animals were sacrificed, brains removed and cooled to −70° C. Thereafter, the brains were sectioned in 20 mm thick sections of which 5–7 with hippocampal tissue were selected and stained with hematoxylin eosine (HE).

Figure 1:
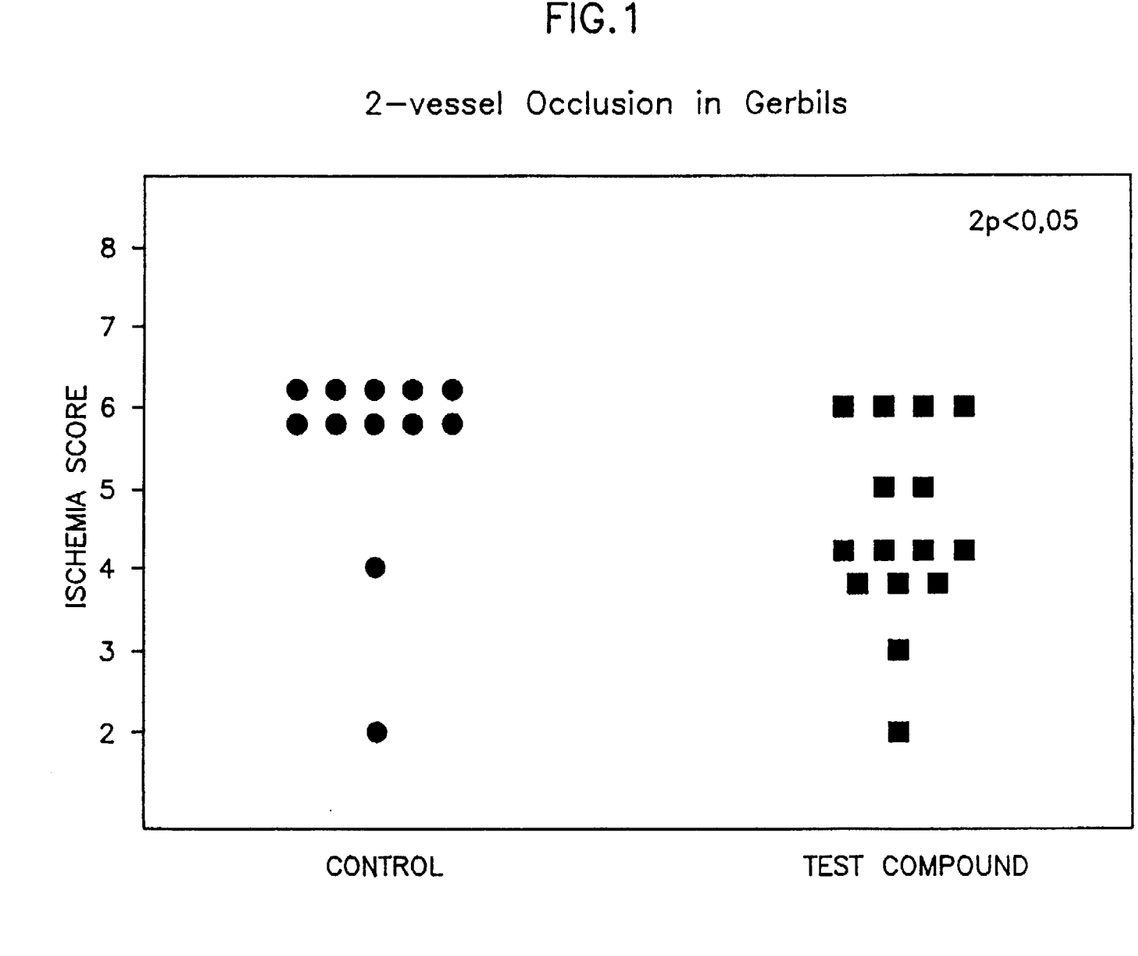

Based upon the degree of hippocampal damage, each hippocampus was categorised into one of four groups (Group 1: no damage in the CA1-layer; Group 2: the CA1-layer partly damaged; Group 3: the CA1-layer completely damaged; and Group 4: damage in more than just the CA1-layer). The total ischemic score was obtained as the sum of the right and left scores, thus resulting in ischaemic scores ranging from 2 to 8. Mann-Whitney Rank Sum Test was used for statistical evaluation. The test results are presented in FIG. 1.

The compound, 8-methyl-5-(4-(N,N-dimethylsulphamoyl)phenyl)-6,7,8,9-tetrahydro-1H-pyrrolo[3,2-h]isoquinoline-2,3-dione-3-oxime showed significant neuroprotective effect in the gerbil 2-VO model.

Pharmaceutical Compositions

While it is possible that, for use in therapy, a compound of the invention may be administered as the raw chemical, it is preferable to present the active ingredient as a pharmaceutical formulation.

The invention thus further provides pharmaceutical formulations comprising a compound of the invention or a pharmaceutically acceptable salt or derivative thereof together with one or more pharmaceutically acceptable carriers therefor and, optionally, other therapeutic and/or prophylactic ingredients. The carrier(s) must be "uacceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparation s can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising the active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump.

Administration to the respiratory tract may also be achieved by means of an aerosol formulation in which the active ingredient is provided in a pressurized pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

METHOD OF TREATING

The compounds of this invention are extremely useful in the treatment of central nervous system disorders related to their biological activity. The compounds of this invention may accordingly be administered to a subject, including a human, in need of treatment, alleviation, or elimination of a disorder or disease associated with the biological activity of the compounds. This includes especially excitatory amino acid dependent, including glutamate and/or aspartate dependent psychosis, excitatory amino acid dependent, including glutamate and/or aspartate dependent anoxia, excitatory amino acid dependent, including glutamate and/or aspartate dependent ischemia, excitatory amino acid dependent, including glutamate and/or aspartate dependent Parkinsonism, excitatory amino acid dependent, including glutamate and/or aspartate dependent convulsions and excitatory amino acid dependent, including glutamate and/or aspartate dependent migraine as well as ALS. Suitable dosage ranges are 0.1 to 1000 milligrams daily, 10–500 milligrams daily, and especially 30–100 milligrams daily, dependent as usual upon the exact mode of administration, form in which administered, the indication toward which the administration is directed, the subject involved and the body weight of the subject involved, and further the preference and experience of the physician or veterinarian in charge.

The following nonlimiting examples illustrate the present invention further.

Example 1

A solution of 4-acetamido-2-methyl-2H-1,3-dihydroisoindole (10 g) and bromine (3.0 g) in trifluoroacetic acid (150 ml) was stirred at 50° C. for 40 hours. The solution was evaporated in vacuo. The residue was dissolved in water (300 ml), and pH was adjusted to neutral with sat. $Na_2CO_3$. This treatment afforded a crystalline precipitate of the product, which was collected by filtration. Yield 9 g, mp. 145°–148°.

In a similar manner the following compound was prepared:

2-methyl-5-acetamido-8-bromo-1,2,3,4-tetrahydroisoguinoline.

Example 2

A solution of potassium nitrate (1.78 g, 8.56 mmol) in 2 ml concentrated $H_2SO_4$ was added slowly to a solution of 5-bromoisoquinoline in 12 mL concentrated $H_2SO_4$. After stirring for 3 hours the reaction mixture was poured onto ice and neutralized with conc. ammonium hydroxide. The yellow precipitate was extracted with ethyl acetate (3×), and the combined organic layers were washed with saturated NaCl, dried over $MgSO_4$, filtered and concentrated. The residue was chromatographed on silica gel (40% ethyl acetate in hexane as eluent) to give 5-bromo-8-nitroisoquinoline.

Example 3

A mixture of 5-bromo-8-nitroisoquinoline (0.99 g, 3.91 mmol) and dimethylsulfate (0.41 mL) in anhydrous DMF (20 mL) was heated at 80° C. for 24 hours. After removing the DMF in vacuo, the isoquinoline methylammonium salt was obtained (used without further purification).

In a similar manner the following compound was prepared:

2-Ethyl-5-bromo-8-nitroquinolinium ethylsulphate by reaction with diethyl sulphate

Example 4

The isoquinolinium salt (3.9 mmol) was dissolved in acetic acid (10 mL) and sodium borohydride (0.15 g, 3.97 mmol) was added. After stirring for 24 h, the reaction mixture was diluted with a mixture of ethyl acetate and water and potassium carbonate was added portionwise to neutralize the acetic acid. The aqueous layer was extracted with ethyl acetate (2×), washed with saturated NaCl, dried over $MgSO_4$, filtered and evaporated. The residue was chromatographed on silica gel (30% ethyl acetate in hexane as eluent) to give the light sensitive 2-methyl 5-bromo-8-nitro-1,2,3,4-tetrahydroisoquinoline (0.47 g, 45% yield).

5-Bromo-2-ethyl-8-nitro-1,2,3,4-tetrahydroisoquinoline was prepared according to the same procedure. M.p. 52°–53° C.

Example 5

To a +20° C. cold stirred solution of 2-bromo-N,N-dimethyl-benzene sulphonamide (12.5 g) in diethyl ether (150 ml), butyl lithium (20 ml, 2.5M in hexane) was dropwise added. After the addition, the mixture was stirred for 15 min, and then cooled to +50° C., whereafter tributylborate (16.7 g) was added over a 10 min time period. The reaction mixture was now allowed to attain to room temperature. Hydrochloric acid (1N, 65 ml) was added. The organic phase was washed with aq-NaOH (2N 3×20 ml) the combined aqueous phase was then acidified (HCl) which afforded a crystalline precipitate of the product. Yield 7.6 g.

Example 6

A mixture of 4-acetamido-7-bromo-2-methyl-2H-1,3-dihydro-isoindole (0.2g), phenyl boronic acid (137 mg), tetrakis(triphenylphosphine)palladium [0](26 mg), NaHCO₃, (315 mg) was stirred at reflux temperature in a mixture of water (3.75 ml) and dimethoxyethane (7.5 ml) for 90 min. After cooling to room temperature the reaction mixture was partitioned between EtOAc (25 ml) and aq. NaOH (2×5 ml 1N). The organic phase was then dried over Na₂SO₄ and evaporated to give 4-acetamido-7-phenyl-2-methyl-2H-1,3-dihydro-isoindole, mp 160°–62° C.

In a similar manner the following compounds were prepared from the appropriate bromides and boronic acids:

4-Acetamido-2-ethyl-7-phenyl-2H-1,3-dihydro-isoindole, mp. 67°–68° C.

4-Acetamido-2-methyl-5-nitro-7-phenyl-2H-1,3-dihydro-isoindole mp. 270°–72°C.

5-Acetamido-2-methyl-6-nitro-8-phenyl-1,2,3,4-tetrahydro-isoquinoline mp. 214°–217° C.

2-Methyl-8-nitro-5-phenyl-1,2,3,4-tetrahydro-isoquinoline mp 75°–78° C. from reaction between phenyl boronic acid and 5-bromo-2-methyl-8-nitro-1,2,3,4-tetrahydro-isoquinoline.

5-(4-Carboethoxyphenyl)-2-methyl-8-nitro-1,2,3,4-tetrahydro-isoquinoline, mp 160°–162° C. from reaction between 4-carboethoxyphenyl boronic acid and 5-bromo-2-methyl-8-nitro-1,2,3,4-tetrahydro-isoquinoline.

5-acetamido-2-methyl-8-phenyl-1,2,3,4-tetrahydro-isoquinoline, m.p. 140°–143° C.

2-methyl-8-nitro-5-(2-(N,N-dimethylsulphamoyl)-phenyl)-1,2,3,4-tetrahydro-isoquinoline.

2-methyl-8-nitro-5-(4-(N,N-dimethyicarbamoyl)phenyl)-1,2,3,4-tetrahydro-isoquinoline.

Example 7

4-Acetamido-2-methyl-7-phenyl-2H-1,3-dihydro-isoindole(2.6 g) was stirried at 80° C. for 48 hours in sulphuric acid (66%, 25 mL), whereafter the solution was poured onto ice and then neutralized with aq. NaOH. The precipitated product was collected by filtration, and washed with water. Mp. 154°–55° C.

Deacetylations in a similar manner gave:

4-Amino-2-methyl-5-nitro-7-phenyl-2H-1,3-dihydro-isoindole, mp 170°–72° C.

5-Amino-2-methyl-6-nitro-8-phenyl-1,2,3,4-tetrahydro-isoquinoline, mp. 128°–130° C.

4-Amino-2-ethyl-7-phenyl-2H-1,3-dihydro-isoindole hydrochloride, mp. 222°–225° C.

5-amino-2-methyl-8-phenyl-1,2,3,4-tetrahydroisoquinoline, m.p. 273°–275° C.

Example 8

4,5-Diamino-7-phenyl-2-methyl-2H-1,3-dihydro-isoindole, mp. 230°–240° C. (decomposes),

5,6-Diamino-2-methyl-8-phenyl-1,2,3,4-tetrahydro-isoquinoline,

8-Amino-2-methyl-5-phenyl-1,2,3,4-tetrahydro-isoquinoline hydrochloride, mp. 210°–21° C., 8-amino-2-methyl-5-(2-(N,N-dimethylsulphamoyl) phenyl)-1,2,3,4-tetrahydro-isoquinoline, 8-amino-2-methyl-5-(4-(N,N-dimethylcarbamoyl)phenyl)-1,2,3,4-tetrahydro-isoquinoline, and

5-(4-carboethoxyphenyl)-2-methyl-8-amino-1,2,3,4-tetrahydro-isoquinoline.

Example 9

Example 10 were all obtained by hydrogenation using Pd/C(5%) as catalysist and ethanol as solvent.

A mixture of 4-amino-7-phenyl-2-methyl-2H-1,3-dihydro-isoindole (2.0 g, 9 mmol), conc HCl (0.83 ml), 1.5 ml chloral, 10 g of $Na_2SO_4$, $NH_2OH$ (2.0 g) in water (60 mL) was refluxed for two hours, whereafter it was cooled and neutralized with sat. $NaHCO_3$. The aqueous solution was decanted from the oily residue which was dissolved in methylene chloride (100 mL). This solution was dried over $Na_2SO_4$, and the solvent was removed by evaporation. The residue was dissolved in methane suiphonic acid (3 ml) and heated to 120° C. for 30 min. After cooling to ambient temperature the solution was diluted with water(20 mL) and neutralized with sat. $Na_2CO_3$. The impure product was filtered off. Pure 7-methyl-5-phenyl-1,6,7,8-tetrahydrobenzo[2,1-b:3,4-c]dipyrrole-2,3-dione mp. 187°–90° C. was obtained after column purification on silica gel using methylene chloride acetone methanol (4:1:1) as eluent.

In a similar manner the following compounds were prepared from the appropriate anilines:

7-Ethyl-5-phenyl-1,6,7,8-tetrahydrobenzo[2,1-b:3,4-c]dipyrrole-2,3-dione, mp. >250 ° C.(decomposes).

8-Methyl-5-phenyl-6,7,8,9-tetrahydro-1H-pyrrolo[3,2-h]isoquinoline-2,3-dione, mp. 280°–82° C.

8-Methyl- 5-(4-carboethoxyphenyl)-6,7,8,9-tetrahydro-1H-pyrrolo[3,2-h]isoquinoline-2,3-dione, mp dec. o.180° C.

7-Methyl-5-phenyl-6,7,8,9-tetrahydro-1H-pyrrolo[2,3-f]isoquinoline-2,3-dione, m.p. >300° C.

8-methyl-5-(2-(N,N-dimethylsulphamoyl) phenyl)-6,7,8,9-tetrahydro-1H-pyrrolo[3,2-h]-isoquinoline-2,3-dione.

8-methyl-5-(4-(N,N-dimethylcarbamoyl)phenyl)-6,7,8,9-tetrahydro-1H-pyrrolo[3,2-h]-isoquinoline-2,3-dione, m.p. dec o. 190° C.

Example 10

4 g of 8-methyl-5-phenyl-6,7,8,9-tetrahydro-1H-pyrrolo [3,2-h]isoquinoline-2,3-dione was added in portions to ice-cold chlorosulphonic acid (20 ml). The solution was allowed to stir at room temperature for ½ hour before it was cooled on ice. Excess chlorosulphonic acid was then destroyed carefully with water. After addition of 40 ml of water a heavy precipitate of the sulphonyl chloride was obtained. This solid was filtered off and washed with water whereafter, without drying, it was dissolved in tetrahydrofuran (100 ml). To this solution was dropwise added a solution of dimethylamine in tetrahydrofuran(100ml, 0.5M). The final mixture was stirred at room temperature for 3 hours and then evaporated. The oily residue was partitioned between water/ Ethyl acetate. The organic phase was extracted with 100 ml 0.5N hydrochloric acid. The aqueous phase was separated and pH adjusted to 9. This caused a precipitate of crude product which could be purified by column cromatography. m.p.>300° C. (decomposes).

In a similar manner the following compounds are prepared:

8-Methyl-5-(4-sulphamoylphenyl)-6,7,8,9-tetrahydro-1H-pyrrolo[3,2-h]isoquinoline-2,3-dione, m.p.>300° C. (decomposes).

8-Methyl-5-(4-(N,N-bis(2-hydroxyethyl)sulphamoyl) phenyl)-6,7,8,9-tetrahydro-1H-pyrrolo[3,2-h]isoquinoline-2,3-dione, m.p.>300° C. (decomposes).

7-Ethyl-5-(4-sulphamoylphenyl)-1,6,7,8-tetrahydrobenzo [2,1 -b:3,4-c]dipyrrole-2,3-dione hydrochloride.

8-methyl-5-(4-(N-t-butylsulphamoyl)phenyl)-6,7,8,9-tetrahydro-1H- pyrrolo[3,2-h]-isoquinoline-2,3-dione, m.p.>300° C.

8-methyl-5-(4-(morpholinosulfonyl)phenyl)-6,7,8,9-tetrahydro-1H-pyrrolo[3,2-h]-isoquinoline- 2,3-dione, m.p. 220° C. (decomposes).

8-methyl-5-(4-(N-(2-hydroxyethyl)sulphamoyl)phenyl)-6,7,8,9-tetrahydro-1H-pyrrolo[3,2-h]isoquinoline-2,3-dione, m.p.>300° C. (decomposes).

8-methyl-5-(4-(4-(2-hydroxyethyl)piperazinosulfonyl) phenyl)-6,7,8,9-tetrahydro-1H-pyrrolo[3,2-h]-isoquinoline-2,3-dione. m.p.>300° C. (decomposes).

8-5(4(N,N-di(2-(N,N-diethylamino)ethyl)-sulphamoyl)-phenyl)-6,7,8,9-tetrahydro-1H-pyrrolo[3,2-h]-isoquinoline-2,3-dione.

8-methyl-5-(4-(piperidinosulfonyl)-phenyl)-6,7,8,9-tetrahydro-1H-pyrrolo[3,2-h]-isoquinoline-2,3-dione. m.p.>300° C. (decomposes).

8-methyl-5-(4-(N-phenysulphamoyl)-phenyl)-6,7,8,9-tetrahydro-1H-pyrrolo[3,2-h]-isoquinoline-2,3-dione. m.p.>300° C. (decomposes).

8-methyl-5-(4-(N,N-diethylsulphamoyl)-phenyl)-6,7,8,9-tetrahydro-1H-pyrrolo[3,2-h]-isoquinoline-2,3-dione. m.p.>300° C. (decomposes).

8-methyl-5-(4-(N-methyl-N-(2-(N,N-dimethylamino)-ethyl)sulphamoyl)-phenyl)-6,7,8,9-tetrahydro-1H-pyrrolo[3,2-h]isoquinoline-2,3-dione. m.p. 265°–270° C. (decomposes 200° C.).

8-methyl-5-(4-(4-(4-chlorophenyl)piperazinosulfonyl)-phenyl)-6,7,8,9-tetrahydro-1H-pyrrolo[3,2-h]-isoquinoline-2,3-dione 8-methyl-5-(4-(4-(3,4-methylenedioxybenzyl)-piperazinosulfonyl)phenyl)-6,7,8,9-tetrahydro-1H-pyrrolo[3,2-h]-isoquinoline-2,3-dione. m.p. 271°–275° C. (decomposes 160° C.).

8-methyl-5-(4-(N-(ethoxycarbonylmethyl)sulphamoyl)-phenyl)-6,7,8,9-tetrahydro-1H-pyrrolo[3,2-h]isoquinoline-2,3-dione. m.p.>300° C. (decomposes).

7-methyl-5-(4-(morpholinosulfonyl)phenyl)-6,7,8,9-tetrahydro-1H-pyrrolo[2,3-f]isoquinoline-2,3-dione, m.p. 220°–260° C. (decomposes.

7-ethyl-5-(4-(morpholinosulfonyl)phenyl)-1,6,7,8-tetrahydrobenzo[1,2-b:3,4-c]dipyrrole-2,3-dione.

7-ethyl-5-(4-(N,N-dimethylsulphamoyl)phenyl)-1,6,7,8-tetrahydrobenzo[1,2-b:3,4-c]dipyrrole-2,3-dione.

8-methyl-5-(4-(N,N-dibenzylsulphamoyl)-phenyl)-6,7,8,9-tetrahydro-1H-pyrrolo[3,2-h]-isoquinoline-2,3-dione.

Example 11

-continued

The product of Example 10 (150 mg), NH$_2$OH, CH$_3$SO$_3$H (100 mg) was stirred one hour at reflux temperature in ethanol (5 ml) whereafter the precipitated product was filtered off. Mp. 242°–243° C.

In a similar manner the following compounds are prepared:

8-methyl-5-(4-sulphamoylphenyl)-6,7,8,9-tetrahydro-1H-pyrrolo[3,2-h]isoquinoline-2,3-dione 3-oxime, mesylat, m.p. 280°–82° C.

8-methyl-5-(4-(N,N-bis(2-hydroxyethyl)sulphamoyl) phenyl)-6,7,8,9-tetrahydro-1H-pyrrolo[3,2-h]isoquinoline-2,3-dione-3-oxime, hydrochloride, mp>300° C.

7-ethyl-5-(4-sulphamoylphenyl)-1,6,7,8-tetrahydrobenzo [2,1-b:3,4-c]dipyrrole-2,3-dione 3-oxime hydrochloride.

8-Methyl- 5-(4-carboethoxyphenyl)-6,7,8,9-tetrahydro-1H-pyrrolo[3,2-h]isoquinoline-2,3-dione-3-oxime, mp>200° C. (decomposes).

8-methyl-5-(4-(N,N-dimethylsulphamoyl)phenyl)-6,7,8, 9-tetrahydro-1H-pyrrolo[3,2-h ]-isoquinoline-2,3-dione-3-O-methyloxime, hydrochloride, m.p. 280° C. (decomposes).

8-methyl-5-(4-(N-t-butylsulphamoyl)phenyl)-6,7,8,9-tetrahydro-1H-pyrrolo[3,2-h]-isoquinoline-2,3-dione-3-oxime, m.p.>300° C.

8-methyl-5-(4-(morpholinosulfonyl)phenyl)-6,7,8,9-tetrahydro-1H-pyrrolo[3,2-h]-isoquinoline-2,3-dione-3-oxime, mesylat, m.p. 260°–65° C.

8-methyl-5-(4-(N-(2-hydroxyethyl)sulphamoyl)phenyl)-6,7,8,9-tetrahydro-1H-pyrrolo[3,2-h]isoquinoline-2,3-dione-3-oxime, hydrochloride, m.p. 260° C. (decomposes).

8-methyl-5-(4-(N,N-dimethylcarbamoyl)phenyl)-6,7,8,9-tetrahydro-1H-pyrrolo[3,2-h ]-isoquinoline-2,3-dione-3-oxime, mesylat, m.p. 247° C. (decomposes).

8-methyl-5-(4-(4-(2-hydroxyethyl)piperazinosulfonyl) phenyl)-6,7,8,9-tetrahydro-1H-pyrrolo[3,2-h]-isoquinoline-2,3-dione-3-oxime, dimesylate tetrahydrate, m.p. 190° C. (decomposes).

8-methyl-5-(4-(N,N-dimethylsulphamoyl)phenyl)-6,7,8, 9-tetrahydro-1H-pyrrolo[3,2h]-isoquinoline-2,3-dione-3-O-t-butyloxime, hydrochloride, m.p. 285° C. (decomposes).

8-methyl-5-(4-(N,N-di(2-(N,N-diethylamino)ethyl)-sulphamoyl)-phenyl)-6,7,8,9-tetrahydro-1H-pyrrolo[3,2-h]-isoquinoline-2,3-dione-3-oxime, m.p.>300° C.

8-methyl-5-(4-(piperidinosulfonyl)-phenyl)-6,7,8,9-tetrahydro-1H-pyrrolo[3,2-h]-isoquinoline-2,3-dione-3-oxime, mesylate, m.p. 270° C. (decomposes).

8-methyl-5-(4-(N-phenylsulphamoyl)-phenyl)-6,7,8,9-tetrahydro-1H-pyrrolo[3,2-h]-isoquinoline-2,3-dione-3-oxime, mesylate trihydrate, m.p. 238°–40° C.

8-methyl-5-(4-(N,N-diethylsulphamoyl)-phenyl)-6,7,8,9-tetrahydro-1H-pyrrolo[3,2-h]-isoquinoline-2,3-dione-3-oxime, mesylate, m.p. 270°–275° C. (decomposes).

8-methyl-5-(4-(N-methyl-N-(2-(N,N-dimethylamino)-ethyl)sulphamoyl)-phenyl) -6,7,8,9-tetrahydro-1H-pyrrolo[3,2-h]isoquinoline-2,3-dione-3-oxime, dimesylate, gas evolution 75°–80° C.

8-methyl-5-(4-(4-(4-chlorophenyl)piperazinosulfonyl)-phenyl)-6,7,8,9-tetrahydro-1H-pyrrolo[3,2-h]-isoquinoline-2,3-dione-3-oxime, mesylate, m.p.>300.

8-methyl-5-(4-(4-(3,4-methylenedioxybenzyl)-piperazinosulfonyl)phenyl)-6,7,8,9-tetrahydro-1H-pyrrolo[3,2-h]-isoquinoline-2,3-dione-3-oxime, dimesylate, m.p. 175°–180° C.

8-methyl-5-(4-(N-(ethoxycarbonylmethyl)sulphamoyl)-phenyl)-6,7,8,9-tetrahydro-1H-pyrrolo[3,2-h]isoquinoline-2,3-dione-3-oxime, m.p.>300° C.

7-methyl-5-(4-(morpholinosulfonyl)phenyl)-6,7,8,9-tetrahydro-1H-pyrrolo[2,3-f]isoquinoline-2,3-dione-3-oxime, mesylate, m.p. 220°–260° C. (decomposes).

7-methyl-5-(4-(morpholinosulfonyl)phenyl)-6,7,8,9-tetrahydro-1H-pyrrolo[2,3-f]isoquinoline-2,3-dione-3-O-methyloxime, hydrochloride, m.p.>300° C.

7-ethyl-5-(4-(morpholinosulfonyl)phenyl)-1,6,7,8-tetrahydrobenzo[1,2-b:3,4-c]dipyrrole-2,3-dione-3-oxime, mesylate, m.p. 220°–240° C.

7-ethyl-5-(4-(N,N-dimethylsulphamoyl)phenyl)-1,6,7,8-tetrahydrobenzo[1,2-b:3,4-c]dipyrrole-2,3-dione-3-oxime, mesylate, m.p.>300° C.

8-methyl-5-(4-(N,N-dibenzylsulphamoyl)-phenyl)-6,7,8,9-tetrahydro- 1H-pyrrolo[3,2h]-isoquinoline-2,3-dione-3-oxime, mesylate.

8-methyl-5-(2-(N,N-dimethylsulphamoyl)phenyl)-6,7,8,9-tetrahydro-1H-pyrrolo[3,2h]-isoquinoline-2,3-dione-3-oxime, m.p. 264° C. (decomposes).

We claim:

1. A compound having the formula or a pharmaceutically acceptable salt thereof
wherein $R^1$ is hydrogen, alkyl or benzyl;

X is O or $NOR^2$, wherein $R^2$ is hydrogen, alkyl or benzyl;

Y is N—$R^4$ wherein $R^4$ is hydrogen, OH or alkyl;

n is 0 or 1;

$R^6$ is phenyl which is substituted one or more times with substituents selected from the group consisting of $SO_2NR'R''$, $CONR'R''$, and $COR'''$
wherein R' and R'' each independently are hydrogen, alkyl, or —$(CH_2)_p$—W, wherein p is 0, 1, 2, 3, 4, 5, or 6, and W is hydroxy, amino, alkoxycarbonyl, or phenyl which may be substituted one or more times with substituents selected from the group consisting of halogen, $CF_3$, $NO_2$, amino, alkyl, alkoxy or methylenedioxy; or wherein R' and R'' together is $(CH_2)_r Z(CH_2)_s$ wherein r and s each independently are 0, 1, 2, 3, 4, 5, or 6 and Z is O, S, $CH_2$ or NR'''' wherein R'''' is hydrogen, alkyl, or —$(CH_2)_p$—W, wherein p is 0, 1, 2, 3, 4, 5, or 6, and W is hydroxy, amino, alkoxycarbonyl, or phenyl which may be substituted one or more times with substituents selected from the group consisting of halogen, $CF_3$, $NO_2$, amino, alkyl, alkoxy or methylenedioxy;

and wherein R''' is hydrogen, alkyl, alkoxy or phenyl which may be substituted one or more times with substituents selected from the group consisting of halogen, $CF_3$, $NO_2$, amino, alkyl, alkoxy or methylenedioxy;

A is a ring of five to seven atoms fused with the benzo ring at the positions marked a and b, and formed by the following bivalent radicals:

wherein
$R^{12}$ is hydrogen, $CH_2CH_2OH$, or alkyl.

2. The compound of claim 1 having the formula or a pharmaceutically acceptable salt thereof.

3. The compound of claim 1 having the formula or a pharmaceutically acceptable salt thereof.

4. The compound of claim 1 having the formula or a pharmaceutically acceptable salt thereof.

5. The compound of claim 1 which is 8-methyl-5-(4-(N,N-dimethylsulphamoyl)phenyl)-6,7,8,9-tetrahydro-1H-pyrrolo[3,2h]-isoquinoline-2,3-dione-3-oxime, 8-methyl-5-(4-(sulphamoyl)phenyl)-6,7,8,9-tetrahydro-1H-pyrrolo[3,2-h]-isoquinoline-2,3-dione-3-oxime, 8-methyl-5-(4-(N,N-bis(2-hydroxyethyl)sulphamoyl) phenyl)-6,7,8,9-tetrahydro-1H-pyrrolo[3,2-h] isoquinoline-2,3-dione-3-oxime, 8-methyl-5-(4-(ethoxycarbonyl)phenyl)-6,7,8,9-tetrahydro-1H-pyrrolo[3,2-h]-isoquinoline-2,3-dione-3-oxime, 8-methyl-5-(4-(N,N-dimethylsulphamoyl)phenyl)-6,7,8,9-tetrahydro-1H-pyrrolo[3,2h]-isoquinoline-2,3-dione-3-O-methyloxime, 8-methyl-5-(4-(N-t-butylsulphamoyl)phenyl)-6,7,8,9-tetrahydro-1H-pyrrolo[3,2-h ]-isoquinoline-2,3-dione-3-oxime, 8-methyl-5-(4-(morpholinosulfonyl)phenyl)-6,7,8,9-tetrahydro-1H-pyrrolo[3,2-h]-isoquinoline-2,3-dione-3-oxime, 8-methyl-5-(4-(N-(2-hydroxyethyl)sulphamoyl)phenyl)-6,7,8,9-tetrahydro-1H-pyrrolo[3,2-h]isoquinoline-2,3-dione-3-oxime, 8-methyl-5-(4-(N,N-dimethylcarbamoyl)phenyl)-6,7,8,9-tetrahydro-1H-pyrrolo[3,2-h]-isoquinoline2,3-dione-3-oxime, 8-methyl-5-(4-(4-(2-hydroxyethyl)piperazinosulfonyl) phenyl)-6,7,8,9-tetrahydro-1H-pyrrolo[3,2-h]-isoquinoline-2,3-dione-3-oxime, 8-methyl-5-(4-(N,N-dimethylsulphamoyl)phenyl)-6,7,8,9-tetrahydro- 1H-pyrrolo[3,2h]-isoquinoline-2,3-dione-3-O-t-butyloxime, 8-methyl-5-(4-(morpholinosulfonyl)phenyl)-6,7,8,9-tetrahydro-1H-pyrrolo[3,2-h]-isoquinoline2,3-dione, 8-methyl-5-(4-(N,N-di(2-(N,N-diethylamino)ethyl)-sulphamoyl)-phenyl)-6,7,8,9-tetrahydro-1H-pyrrolo[3,2-h]-isoquinoline-2,3-dione-3-oxime, 8-methyl-5-(4-(piperidinosulfonyl)-phenyl)-6,7,8,9-tetrahydro-1H-pyrrolo[3,2-h]-isoquinoline-2,3-dione-3-oxime, 8-methyl-5-(4-(N-phenylsulphamoyl)-phenyl)-6,7,8,9-tetrahydro-1H-pyrrolo[3,2-h]-isoquinoline-2,3-dione-3-oxime, 8-methyl-5-(4-(N,N-diethylsulphamoyl)-phenyl)-6,7,8,9-tetrahydro-1H-pyrrolo[3,2-h]-isoquinoline-2,3-dione-3-oxime, 8-methyl-5-(4-(N-methyl-N-(2-(N,N-dimethylamino)-ethyl)sulphamoyl)-phenyl)-6,7,8,9-tetrahydro-1H-pyrrolo[3,2-h]isoquinoline-2,3-dione-3-oxime, 8-methyl-5-(4-(4-(4-chlorophenyl)piperazinosulfonyl)-phenyl)-6,7,8,9-tetrahydro-1H-pyrrolo[3,2-h]-isoquinoline-2,3-dione-3-oxime, 8-methyl-5-(4-(4-(3,4-methylenedioxybenzyl)-piperazinosulfonyl)phenyl)-6,7,8,9-tetrahydro-1H-pyrrolo[3,2-h]-isoquinoline-2,3-dione-3-oxime, 8-methyl-5-(4-(N-(ethoxycarbonylmethyl)sulphamoyl)-phenyl)-6,7,8,9-tetrahydro-1H-pyrrolo[3,2-h] isoquinoline-2,3-dione-3-oxime, 7-methyl-5-(4-(morpholinosulfonyl)phenyl)-6,7,8,9-tetrahydro-1H-pyrrolo[2,3-f]isoquinoline-2,3-dione-3-oxime, 7-methyl-5-(4-(morpholinosulfonyl)phenyl)-6,7,8,9-tetrahydro-1H-pyrrolo[2,3-f]isoquinoline-2,3-dione-3-O-methyloxime, 7-ethyl-5-(4-(morpholinosulfonyl)phenyl)-1,6,7,8-tetrahydrobenzo[1,2-b:3,4-c]dipyrrole-2,3-dione-3-oxime, 7-ethyl-5-(4-(N,N-dimethylsulphamoyl)phenyl)-1,6,7,8-tetrahydrobenzo[1,2-b:3,4-c]dipyrrole-2,3-dione-3-oxime, and 8-methyl-5-(4-(N,N-dibenzylsulphamoyl)-phenyl)-6,7,8,9-tetrahydro-1H-pyrrolo[3,2h]-isoquinoline-2,3-dione-3-oxime; the corresponding 2,3-diones;

or a pharmaceutically acceptable salt thereof.

6. A method of treating a disorder or disease of a mammal responsive to glutamic and/or aspartic acid receptor antagonists, which comprises administering to a patient in need thereof an effective amount of a compound of claim 1.

7. The method of claim 6 wherein lathyrism, Alzheimer's disease, Huntington's diseases, ALS, schizophrenia, Parkinsonism, epilepsy, anxiety, pain, drug addiction, or cerebrovascular disorders are treated.

8. A pharmaceutical composition comprising a therapeutically-effective amount of a compound of claim 1 together with at least one pharmaceutically-acceptable carrier or diluent.

9. A method of preparing a compound of claim 1 comprising the step of:

a) reacting a compound having the formula wherein A, a, b $R^1$, Y, n and $R^6$ have the meanings set forth in claim 1, with $NH_2OR^2$, wherein $R^2$ has the meaning set forth in claim 1, or with a reactive derivative thereof, to form a compound of claim 1; or b) reacting a compound having the formula wherein A, a, b $R^1$, and $R^6$ have the meanings set forth above, with oxalic acid or a reactive derivative thereof, to form a compound of claim 1, or c) reacting a compound having the formula wherein A, a, b, and $R^6$ have the meanings set forth above, with chloral or a reactive derivative thereof, to form a compound of claim 1.

10. The method of claim 6 wherein said mammal is a human.

11. The compound of claim 1 wherein alkyl is a straight or branched chain of from one to six carbon atoms or cyclic alkyl from three to seven carbon atoms; alkoxy is O-alkyl and amino is $NH_2$, NH-alkyl or N-(alkyl)$_2$.

12. A method of inhibiting GABA release from neurons comprising exposing neurons to an effective amount of a compound of claim 1.

13. The composition of claim 8, wherein the compound of claim 1 is present at an amount of from about 0.1 to about 100 mg/unit dosage.

14. The method of claim 6 wherein said compound is administered at a dosage of from about 0.1 to about 1000 mg/day.

* * * * *